(12) United States Patent
Esarey et al.

(10) Patent No.: US 10,022,146 B2
(45) Date of Patent: Jul. 17, 2018

(54) POWER OPERATED ROTARY EXCISION TOOL

(71) Applicant: EXSURCO MEDICAL, INC., Birmingham, OH (US)

(72) Inventors: Bernard J. Esarey, Cleveland, OH (US); Jason A. Sukey, Elyria, OH (US); Jeffrey A. Whited, Amherst, OH (US)

(73) Assignee: Exsurco Medical, Inc., Birmingham, OH (US)

( * ) Notice: Subject to any disclaimer, the term of this patent is extended or adjusted under 35 U.S.C. 154(b) by 0 days.

(21) Appl. No.: 14/725,303

(22) Filed: May 29, 2015

(65) Prior Publication Data

US 2016/0345996 A1    Dec. 1, 2016

(51) Int. Cl.
| | |
|---|---|
| A61B 17/50 | (2006.01) |
| *A61B 17/322* | (2006.01) |
| *A61B 90/00* | (2016.01) |
| *B23P 15/28* | (2006.01) |
| A61B 17/00 | (2006.01) |

(52) U.S. Cl.
CPC ............ *A61B 17/322* (2013.01); *A61B 90/06* (2016.02); *B23P 15/28* (2013.01); *A61B 2017/00398* (2013.01); *A61B 2017/00526* (2013.01); *A61B 2090/033* (2016.02); *A61B 2090/062* (2016.02)

(58) Field of Classification Search
CPC ......... A22B 5/165; A22B 5/16; A61B 17/322; B26B 25/002; B26B 7/00
USPC ............................ 30/276, 347; 606/132, 180
See application file for complete search history.

(56) References Cited

U.S. PATENT DOCUMENTS

| | | |
|---|---|---|
| 324,435 A | 8/1885 | Underwood |
| 941,829 A | 11/1909 | Wallder et al. |
| 1,220,345 A | 3/1917 | Koster |
| 1,374,988 A | 4/1921 | Cooper |
| 1,379,153 A | 5/1921 | Young |
| 1,476,345 A | 9/1922 | McGee |
| 2,123,712 A | 7/1938 | Clark |
| 2,263,431 A | 11/1941 | White |

(Continued)

FOREIGN PATENT DOCUMENTS

| | | |
|---|---|---|
| EP | 0190827 | 8/1986 |
| FR | 1216947 | 4/1960 |

(Continued)

OTHER PUBLICATIONS

US 3,686,403, 09/1972, Bettcher (withdrawn)

(Continued)

*Primary Examiner* — Katherine M Shi
(74) *Attorney, Agent, or Firm* — Tarolli, Sundheim, Covell & Tummino LLP (57) ABSTRACT

An exemplary hand-held, power operated dermatome comprises a blade housing assembly, a skin deflector, an annular rotary knife blade, a cutting plane, and a depth gauge. The rotary knife blade has an inner region, an upper body portion, and a lower cutting portion. The lower cutting portion has an inner surface, an outer surface, and a bottom surface. A cutting edge of the rotary knife blade is formed by the intersection between the inner surface and the bottom surface of the lower cutting portion. The cutting plane of the dermatome is defined by the cutting edge of the rotary knife blade, and the depth gauge is disposed within the inner region of the rotary knife blade.

29 Claims, 9 Drawing Sheets

(56) References Cited

U.S. PATENT DOCUMENTS

| | | | |
|---|---|---|---|
| 2,266,888 A | 12/1941 | McCurdy et al. |
| 2,540,462 A | 2/1951 | Smith |
| 2,582,511 A | 1/1952 | Stryker |
| 2,730,100 A | 1/1956 | Hood |
| 2,827,657 A | 3/1958 | Bettcher |
| 3,126,889 A | 3/1964 | Blumenfield |
| 3,197,808 A | 8/1965 | Mears |
| RE25,947 E | 12/1965 | Bettcher |
| 3,269,010 A | 8/1966 | Bettcher |
| 3,461,557 A | 8/1969 | Behring |
| 3,670,734 A | 6/1972 | Hardy, Jr. |
| 4,082,232 A | 4/1978 | Brewer |
| 4,142,291 A | 3/1979 | Bettcher |
| 4,166,317 A | 9/1979 | Bettcher |
| 4,170,063 A | 10/1979 | Bettcher |
| 4,178,683 A | 12/1979 | Bettcher |
| 4,198,750 A | 4/1980 | Bettcher |
| 4,236,531 A | 12/1980 | McCullough |
| 4,267,759 A | 5/1981 | Sullivan et al. |
| 4,326,361 A | 4/1982 | McGill |
| 4,363,170 A | 12/1982 | McCullough |
| 4,439,924 A | 4/1984 | Bettcher |
| 4,448,101 A | 5/1984 | Templeton |
| 4,492,027 A | 1/1985 | Bettcher |
| 4,494,311 A | 1/1985 | McCullough |
| 4,509,261 A | 4/1985 | Bettcher |
| 4,516,323 A | 5/1985 | Bettcher et al. |
| 4,575,937 A | 3/1986 | McCullough |
| 4,575,938 A | 3/1986 | McCullough |
| 4,590,676 A | 5/1986 | Bettcher |
| 4,609,227 A | 9/1986 | Wild et al. |
| 4,637,140 A | 1/1987 | Bettcher |
| 4,829,860 A | 5/1989 | VanderPol |
| 4,854,046 A | 8/1989 | Decker et al. |
| 4,858,321 A | 8/1989 | McCullough |
| 4,909,640 A | 3/1990 | Nakanishi |
| 5,099,721 A | 3/1992 | Decker et al. |
| 5,163,288 A | 11/1992 | Doley |
| 5,230,154 A | 7/1993 | Decker et al. |
| 5,331,877 A | 7/1994 | Ishii |
| 5,419,619 A | 5/1995 | Lew |
| 5,522,142 A | 6/1996 | Whited |
| 5,529,532 A | 6/1996 | Desrosiers |
| 5,632,090 A | 5/1997 | Smith |
| 5,664,332 A | 9/1997 | Whited et al. |
| 5,692,307 A | 12/1997 | Whited et al. |
| 5,761,817 A | 6/1998 | Whited et al. |
| 5,940,972 A | 8/1999 | Baris et al. |
| 5,971,413 A | 10/1999 | Kassouf |
| 6,070,945 A | 6/2000 | Ritchey et al. |
| 6,327,783 B1 | 12/2001 | Ming |
| 6,354,949 B1 | 3/2002 | Baris et al. |
| 6,460,254 B1 | 10/2002 | Mori et al. |
| 6,604,288 B2 | 8/2003 | Whited et al. |
| 6,615,494 B2 | 9/2003 | Long et al. |
| 6,665,943 B1 | 12/2003 | Sloane et al. |
| 6,694,649 B2 | 2/2004 | Whited et al. |
| 6,751,872 B1 | 6/2004 | Whited et al. |
| 6,769,184 B1 | 8/2004 | Whited |
| 6,857,191 B2 | 2/2005 | Whited |
| 6,880,249 B2 | 4/2005 | Long et al. |
| 6,978,548 B2 | 12/2005 | Whited et al. |
| 7,000,325 B2 | 2/2006 | Whited |
| 8,002,779 B2 | 8/2011 | Barker et al. |
| 8,037,611 B2 | 10/2011 | Levsen |
| 8,608,755 B2 | 12/2013 | Mahaffey et al. |
| 8,661,692 B2 | 3/2014 | Whited et al. |
| 8,739,416 B2 | 6/2014 | Mascari et al. |
| 8,752,299 B2 | 6/2014 | Rosu et al. |
| 8,756,819 B2 | 6/2014 | Whited et al. |
| 8,806,761 B2 | 8/2014 | Whited et al. |
| 8,814,881 B2 | 8/2014 | Boles et al. |
| 8,926,632 B2 | 1/2015 | Mahaffey et al. |
| 9,186,171 B2 | 11/2015 | Esarey et al. |
| 9,592,076 B2 | 3/2017 | Esarey et al. |
| 2002/0096027 A1 | 7/2002 | Whited et al. |
| 2003/0070301 A1 | 4/2003 | Herrmann et al. |
| 2003/0084576 A1 | 5/2003 | Whited |
| 2003/0131482 A1 | 7/2003 | Long et al. |
| 2003/0196333 A1 | 10/2003 | Whited |
| 2004/0187316 A1 | 9/2004 | Whited et al. |
| 2004/0211067 A1 | 10/2004 | Whited et al. |
| 2005/0126015 A1 | 6/2005 | Whited |
| 2005/0178009 A1 | 8/2005 | Whited |
| 2005/0217119 A1 | 10/2005 | Rapp |
| 2006/0037200 A1 | 2/2006 | Rosu et al. |
| 2007/0283573 A1 | 12/2007 | Levsen |
| 2007/0283574 A1 | 12/2007 | Levsen |
| 2008/0022537 A1 | 1/2008 | Clarke et al. |
| 2008/0098605 A1 | 5/2008 | Whited et al. |
| 2008/0168667 A1 | 7/2008 | Spinato |
| 2008/0183109 A1 | 7/2008 | Babaev |
| 2008/0137193 A1 | 8/2008 | Whited |
| 2009/0138027 A1 | 5/2009 | Lucas et al. |
| 2009/0157095 A1 | 6/2009 | Barker et al. |
| 2009/0227192 A1 | 9/2009 | Luthi et al. |
| 2010/0101097 A1 | 4/2010 | Thien |
| 2011/0185580 A1 | 8/2011 | Whited |
| 2011/0247220 A1 | 10/2011 | Mascari et al. |
| 2012/0138125 A1 | 6/2012 | Hammermann et al. |
| 2013/0025134 A1 | 1/2013 | Mascari et al. |
| 2013/0025139 A1 | 1/2013 | Whited et al. |
| 2013/0174424 A1 | 7/2013 | Whited et al. |
| 2014/0074118 A1 | 3/2014 | Esarey et al. |
| 2014/0074119 A1 | 3/2014 | Esarey et al. |
| 2014/0074120 A1 | 3/2014 | Esarey et al. |
| 2014/0236180 A1 | 8/2014 | Shafirstein |
| 2016/0106451 A1 | 4/2016 | Esarey |

FOREIGN PATENT DOCUMENTS

| | | |
|---|---|---|
| WO | 1991/17715 A1 | 11/1991 |
| WO | 2004/022290 A1 | 3/2004 |
| WO | 2007/034438 | 3/2007 |
| WO | 2015/195666 A1 | 12/2015 |
| WO | WO2015195666 | 12/2015 |

OTHER PUBLICATIONS

Oct. 3, 2011 Decision and Opinion of the United States Court Appeals for the Federal Circuit (Appeal No. 2011-1038,-1046) regarding the case styled *Bettcher Industries, Inc. v. Bunzl USA, Inc. and Bunzl Processor Distribution, LLC*, Case No. 3:08 CV 2423, U.S. District Court for the Northern District of Ohio, Judge Zouhary.

International Search Report and Written Opinion from PCT/US2011/031196 dated Jun. 17, 2011.

International Search Report and Written Opinion from PCT/US2015/036034 dated Jul. 24, 2015.

European Search Report from European Patent Application No. 11769309.3 dated Aug. 26, 2013.

Ameer, et al., "Evolution of Instruments for Harvest of the Skin Grafts," Indian Journal of Plastic Surgery Jan.-Apr. 2013; 46(1); pp. 28-35.

International Search Report and Written Opinion from PCT/US2016/034370 dated Jul. 29, 2016.

Office Action from U.S. Appl. No. 14/741,012 dated May 10, 2017.

Catalog entitled "Ball Bearing Cages", Publication No. WLK 100 E, Publication Date—Sep. 2004, Pubiished by international Customized Bearings. (34 pages) (Exhibit D).

Operators Manual for Integra Model C Air Dermatome Manufactured by Integra LifeScience Corporation, Copyright 2009, Cincinnati, OH (82 pages) (Exhibit E).

Instruction Manual for Zimmer™ Air Dermatome, Manufactured by Zimmer Surgical, Inc., Dover, OH, Copyright 1992 (127 pages) (Exhibit F).

Operators Manual, Integra TM, Model SB Dermatome, Manufactured by Integra LifeSciences Corporation, Plainsboro, New Jersey, Copyright 2005 (6 pages) (Exhibit G).

(56) References Cited

OTHER PUBLICATIONS

Informational Brochure for Humeca Dermatome Blades, Manufactured by Humeca BV, Enschede, The Netherlands, publication date Oct. 2008 (1 page) (Exhibit H).
Image of Super Gyros Knife-Metal, manufactured by Optimal Automatics, Inc., Chicago, IL. Advertisement [online], Retrieved from the Internet; URL:http://www.autodoner.com/autodoner/products/gyro-knife/super-gyros-knife-metal.aspx.
14 Photographs of Super Gyros Knife, Model P, Manufactured by Optimal Automatics, Inc., Chicago, IL.
3 Photographs of Power Operated Gyros Knife Manufacturer, Unknown.
Image of Super Gyros Knife-Plastic, manufactured by Optimal Automatics, Inc., Chicago, IL. Advertisement [online], Retrieved from the Internet: URL:http://www.autodoner.com/autodoner/products/gyro-knife/super-gyros-knife-plastic.aspx.
Office Action dated May 10, 2017 for U.S. Appl. No. 14/741,012, filed Jun. 16, 2015 (11 pages).
Office Action dated Oct. 19, 2017 for U.S. Appl. No. 14/741,012, filed Jun. 16, 2015 (6 pages).

POWER OPERATED ROTARY EXCISION TOOL

TECHNICAL FIELD

The present invention relates generally to power operated dermatomes, such as rotary knife dermatomes and rotary disc dermatomes.

BACKGROUND OF THE INVENTION

Power operated dermatomes, such as rotary knife dermatomes, are hand-held surgical instruments used by a physician or medical professional to cut thin layers or sections of skin tissue. Dermatomes are used in hospitals and other medical facilities for excising or removal of skin tissue from patients in connection with various medical procedures including split-thickness and full-thickness skin grafting, skin debriding (e.g., removal of burned skin tissue), tumor/lesion removal, and breast reduction, among other procedures. Dermatomes are also used to remove skin tissue from deceased human or animal donors for skin grafting purposes.

Prior power operated dermatomes typically included a reciprocating cutting blade disposed at a front or leading edge of the dermatome with a guard or depth gauge to allow the operator to set a depth of cut to remove a desired thickness of skin tissue. The handle of prior dermatomes was disposed rearward of the cutting direction of the blade. Such dermatome configurations required the operator to move the dermatome away from the his body while cutting, resulting in reduced visibility of the area of skin to be removed, and less precise control of the dermatome.

SUMMARY

Exemplary embodiments of dermatomes, dermatome blades, and dermatome blade housings are herein.

In one exemplary embodiment, a power operated dermatome comprises a blade housing assembly, a skin deflector, an annular rotary knife blade, a cutting plane, and a depth gauge. The rotary knife blade has an inner region, an upper body portion, and a lower cutting portion. The lower cutting portion has an inner surface, an outer surface, and a bottom surface. A cutting edge of the rotary knife blade is formed by the intersection between the inner surface and the bottom surface of the lower cutting portion. The cutting plane of the dermatome is defined by the cutting edge of the rotary knife blade, and the depth gauge is disposed within the inner region of the rotary knife blade.

BRIEF DESCRIPTION OF THE DRAWINGS

These and other features and advantages of the present invention will become better understood with regard to the following description and accompanying drawings in which.

DETAILED DESCRIPTION

Figure 1:
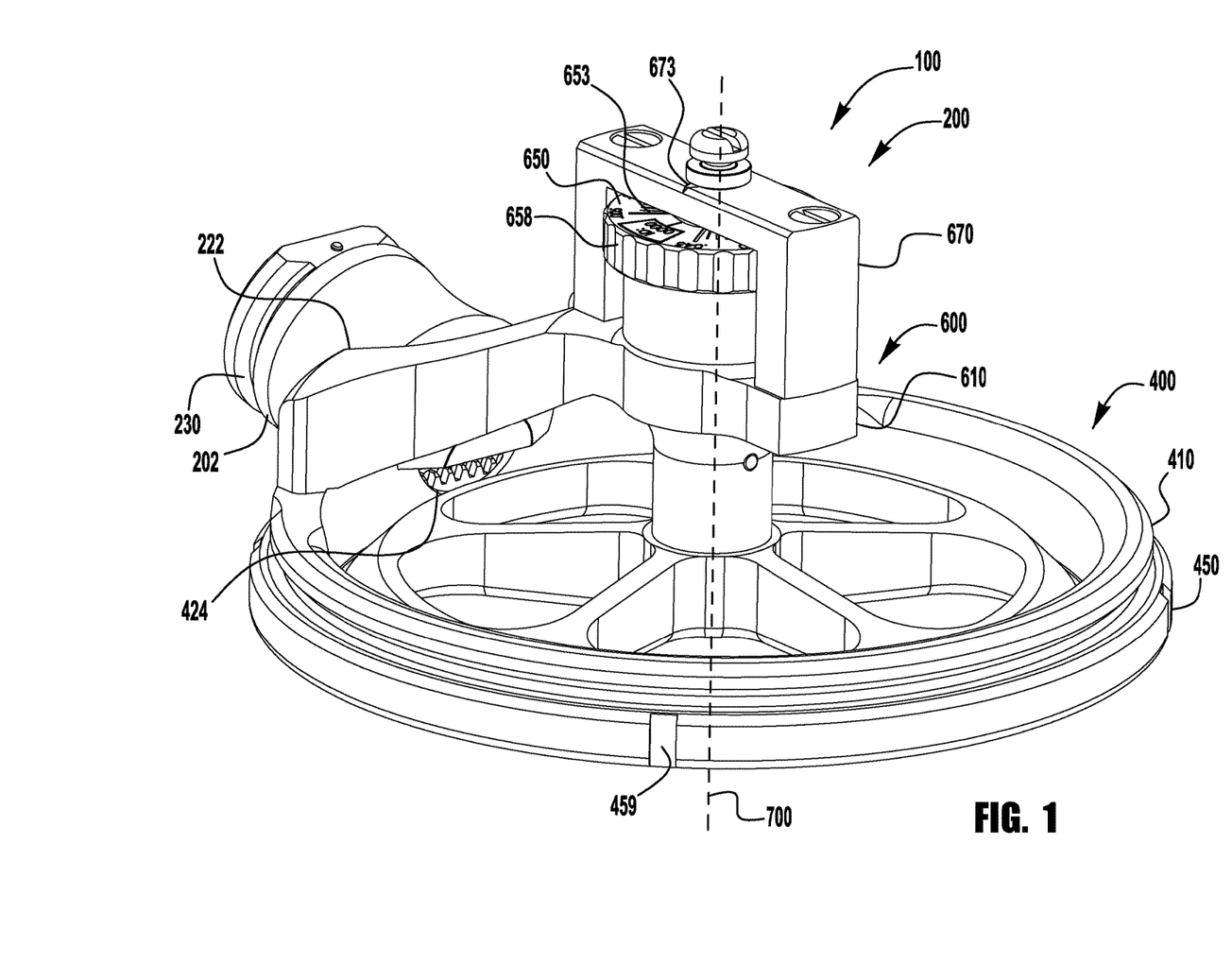
FIG. 1 is a perspective view of an exemplary dermatome.
Figure 2:
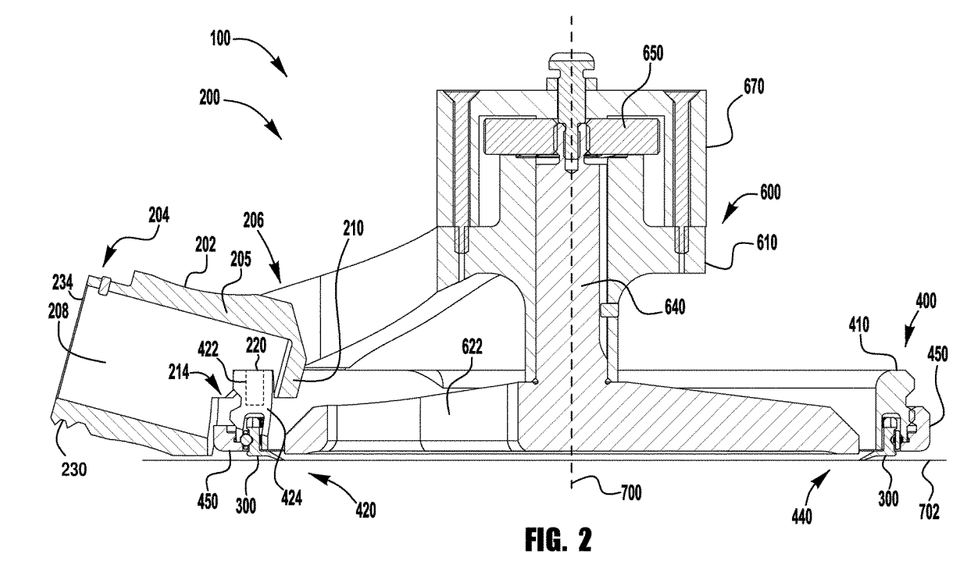
FIG. 2 is a cross-section of the exemplary dermatome of FIG. 1.

FIGS. 1 through 7 illustrate an exemplary embodiment of a head assembly 200 of a hand-held, power operated dermatome 100. The power operated dermatome 100 comprises a handle assembly (not shown), a drive assembly (not shown), and a head assembly 200. The head assembly 200 includes a frame body 202, an annular rotary knife blade 300, a blade housing assembly 400, and a depth gauge 600. The cross-section of FIG. 2 is taken through the above components to more clearly indicate their relative position inside of the head assembly 200 of the dermatome 100.

Figure 6:
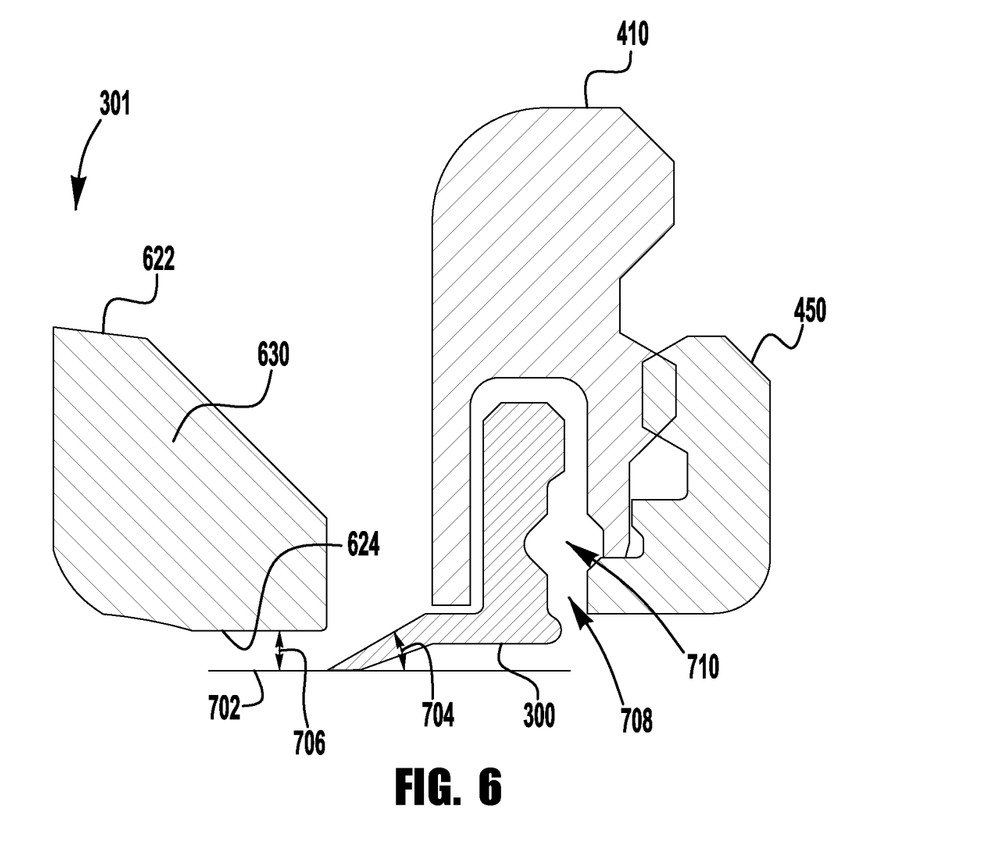
FIG. 6 is an enlarged view of a cross-section of blade housing assembly 400.

During operation of the dermatome 100, the rotary knife blade 300 is driven around an axis of rotation 700 at high rotational speed (on the order of about 500-1,500 RPM) by the drive assembly. As shown in FIG. 6, the cutting edge 360 of the rotary knife blade 300 forms a cutting plane 702 that is substantially orthogonal to axis of rotation 700. A lower blade portion 304 of the rotary knife blade 300 is generally frustoconical in shape, defining a cutting angle 704 with the cutting plane 702. During operation of the dermatome 100, the cutting edge 360 cuts into the skin of a patient at the cutting angle 704 until a bottom surface 624 of the depth gauge plate 622 of the depth gauge assembly 600 contacts the patient's body. An axial distance between the bottom surface 624 and the cutting plane 702 defines a depth of cut 706 that corresponds to a maximum thickness skin excised during use of the dermatome 100. An adjustment knob 650 of the depth gauge assembly 600 allows the user to quickly and precisely set and adjust the axial position of the bottom surface 624, thereby adjusting the depth of cut 706. The depth of cut 706 can be adjusted during a cutting operation to vary the thickness of the portion of skin excised from the patient.

The dermatome 100 operates in a manner similar to that of the power operated dermatome disclosed in U.S. patent application Ser. No. 13/842,224 (hereinafter "the '224 application") filed on Mar. 15, 2013 and entitled Power Operated Dermatome With Shielded Rotary Knife Blade, which is incorporated herein by reference in its entirety.

The frame body 202 connects a handle assembly (not shown) to the blade housing assembly 400 of the head assembly 200. The frame body 202 comprises a generally cylindrical body 205 and includes a rearward handle attachment portion 204 and a forward interface portion 206. The interface portion 206 of the frame body 202 includes an end portion 210. The end portion 210 and the body 205 include an opening 214 configured to receive the interface portion 420 of the annular blade housing 410. The rearward attachment portion 204 includes a threaded outer surface 230 located in the handle attachment portion 204 to attach the frame body 202 to the handle assembly. The head assembly 200 can be attached to the handle assembly by any releasable means, such as with a flange and fasteners, a quarter-turn collar, latches, a compression fit, or the like.

The frame body 202 also includes a gear box housing 208 that houses a gear train (not shown) of the drive assembly. The drive assembly is disposed within the handle assembly and gear box housing 208. The rear opening 234 in the frame body 202 allows the drive assembly to be inserted into the gear box housing 208 of the frame body 202 when the handle assembly is attached to the frame body 202. Exemplary handle and drive assemblies are disclosed in the '224 application.

Figure 3:
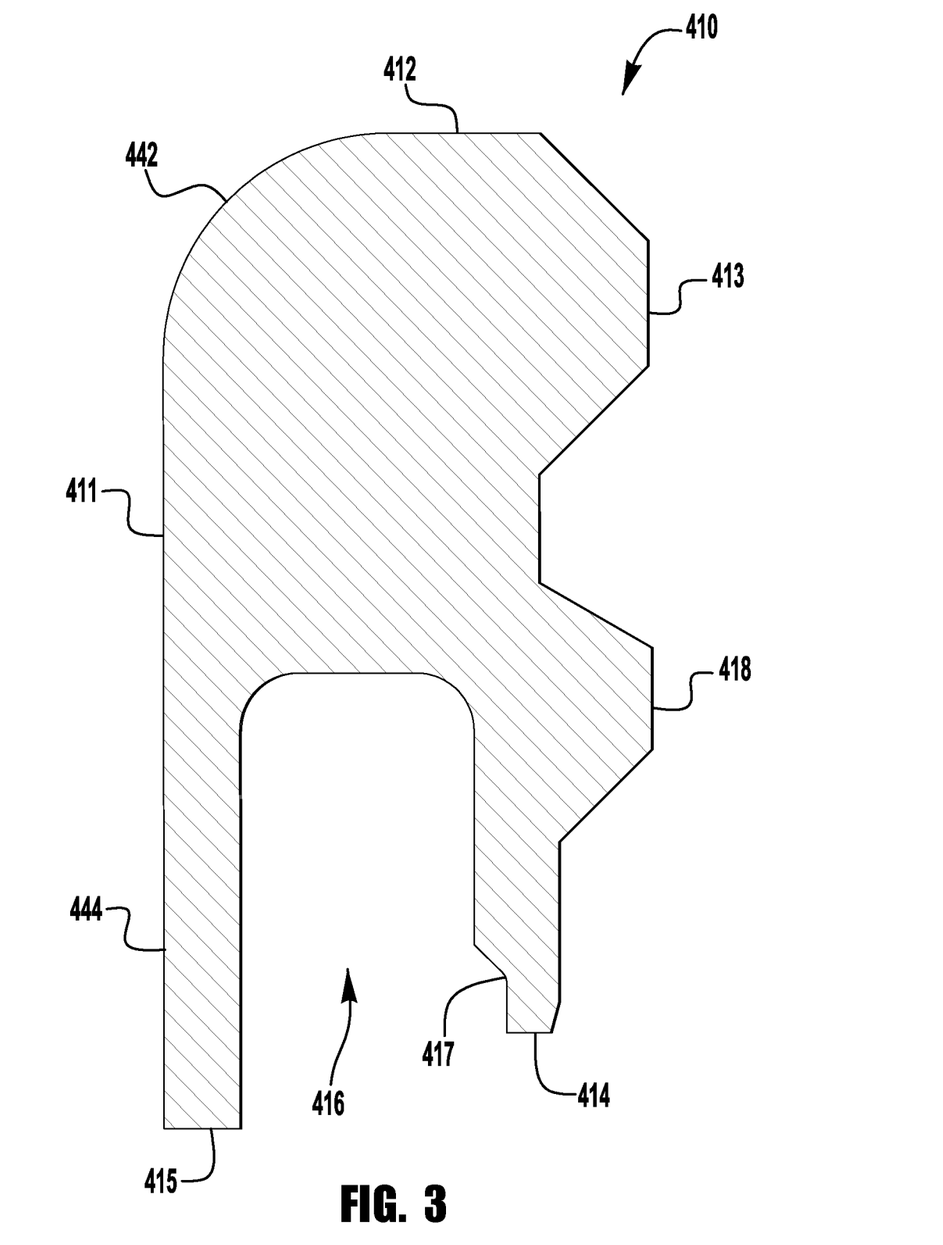
FIG. 3 is an enlarged view of a cross-section of annular blade housing 410.

The blade housing assembly 400 includes an annular blade housing 410 and a lock ring 450. The annular blade housing 410 is generally cylindrical in shape and includes a rear interface portion 420 and a forward skin deflector portion 440. The housing 410 has an inner wall 411 radially spaced apart from an outer wall 413. An outer lower end 414 is axially spaced apart from an upper end 412 and intersects with the outer wall 413. An inner lower end 415 is axially spaced apart from the upper end 412 and intersects with the inner wall 411. An annular blade channel 416 is disposed between the outer and inner lower ends 414, 415. An arcuate bearing surface 417 is located where the outer lower end 414 meets the annular blade channel 416. The outer wall 413 includes a threaded portion 418 for assembly with the lock ring 450.

The interface portion 420 of the annular blade housing 410 includes a gear interface opening 424 that intersects the upper end 412, inner wall 411, and outer wall 413 to expose the driven gear 330 of the rotary knife blade 300 disposed within the annular channel 416. The forward interface portion 206 of the frame body 202 attaches to the interface portion 420 of the housing 410 in the location of the openings 424, 214. The gear interface opening 424 in the blade housing 410 and the opening 214 in the frame body 202 allow the drive train (not shown) within the frame body 202 to interface with the driven gear 330 of the rotary knife blade 300. The interface slot 220 in the forward interface portion 206 of the frame body 202 receives the upper end 412 of the interface portion 420 of the blade housing 410. In one particular embodiment, the frame body 202 is secured to the annular housing 410 with fasteners 222 threaded into threaded openings 422 in the interface portion 420 of the housing 410. The frame body 202 may be attached to the housing 410 by any releasable means, such as with pins, clamps, or the like.

The skin deflector portion 440 of the annular blade housing 410 includes: a blade shield 444 comprising an inner wall 411 and an inner lower end 415; and a rounded guide surface 442 comprising an inner wall 411 and an upper end 412. The blade shield 444 covers the body portion 302 of the rotary knife blade 300 so that the driven gear 330 disposed within the blade channel 416 is not exposed during operation of the dermatome 100. The rounded guide surface 442 is formed at the intersection of the inner wall 411 and upper end 412 and prevents excised skin from tearing as it is removed from the dermatome 100 during operation.

The blade housing assembly 400 further includes a depth gauge support portion 430. The depth gauge support 430 includes one or more ribs 432 that connect the depth gauge assembly 600 and the blade housing assembly 400 to align the center of the depth gauge assembly 600 with the axis of rotation 700. The gauge support portion 430 is integrally part of the blade housing 410, but the gauge support 430 may comprise separate components attached to the blade housing 410 by any means, such as with threaded fasteners, clamps, pins, a welded connection, or the like. The gauge support 430 may also attach to the blade housing 410 in one or more locations, provided that room is left between the ribs 432 in the skin deflector portion 440 of the annular housing 410 for excised skin to be extracted from the dermatome 100 during operation, and provided that the depth gauge assembly 600 is adequately supported during operation of the dermatome 100.

Figure 4:
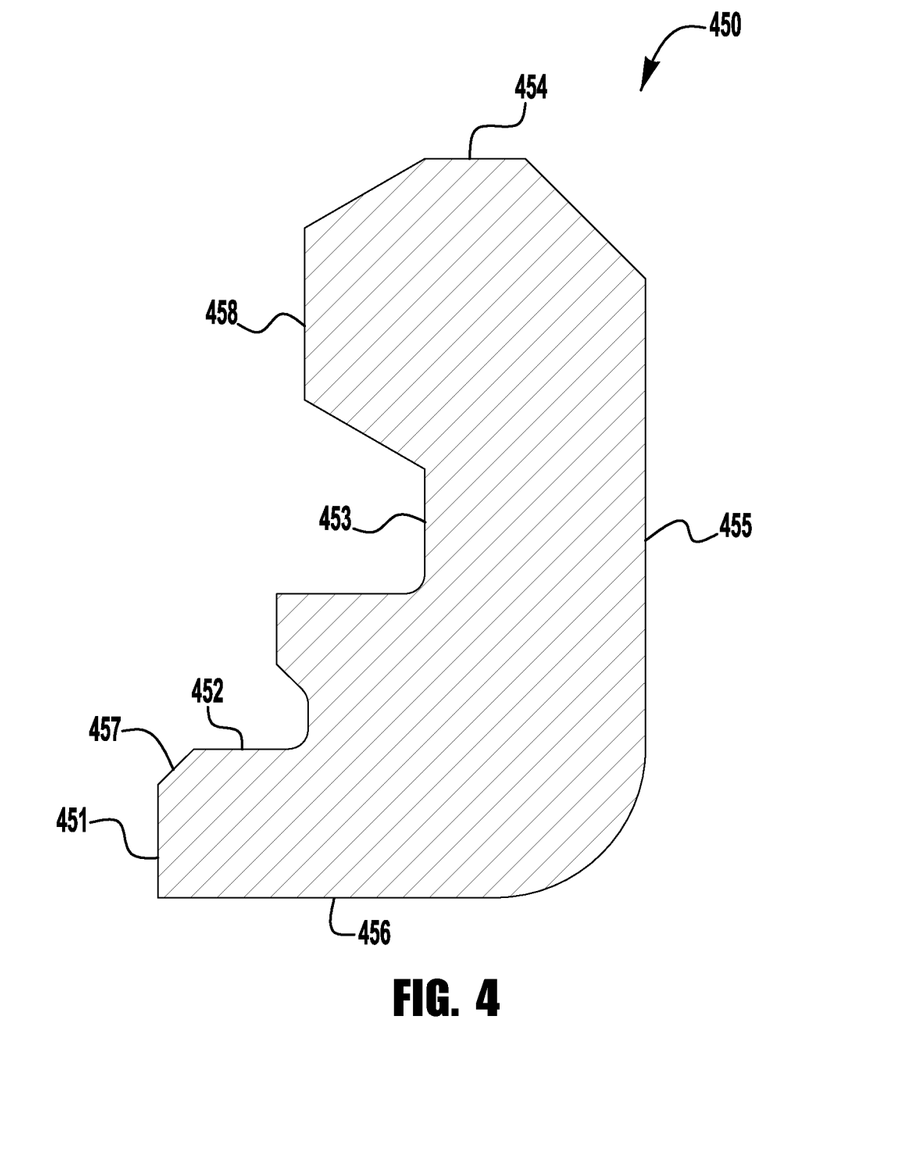
FIG. 4 is an enlarged view of a cross-section of lock ring 450.

The lock ring 450 is generally cylindrical in shape and includes an upper end 454, an axially spaced apart lower end 456, a lower inner surface 451, an upper inner surface 453, and an outer surface 455. The upper and lower inner surfaces 453, 451 are radially spaced apart from the outer surface 455. The lower inner surface 451 is disposed inward of the upper inner surface 453, forming a shoulder 452. An arcuate bearing surface 457 is formed at the intersection of the lower inner surface 451 and the shoulder 452. The upper inner surface 453 includes a threaded portion 458 to assemble the lock ring 450 to the threaded portion 418 of the annular blade housing 410. The outer surface 455 includes peripherally spaced cavities 459 so that the lock ring 450 can be held securely during assembly with the blade housing 410. Though the lock ring 450 is attached to the blade housing 410 with a threaded connection, the lock ring 450 may be attached to the blade housing 410 by any releasable means, such as with threaded fasteners, pins, clamps, or the like.

Figure 5:
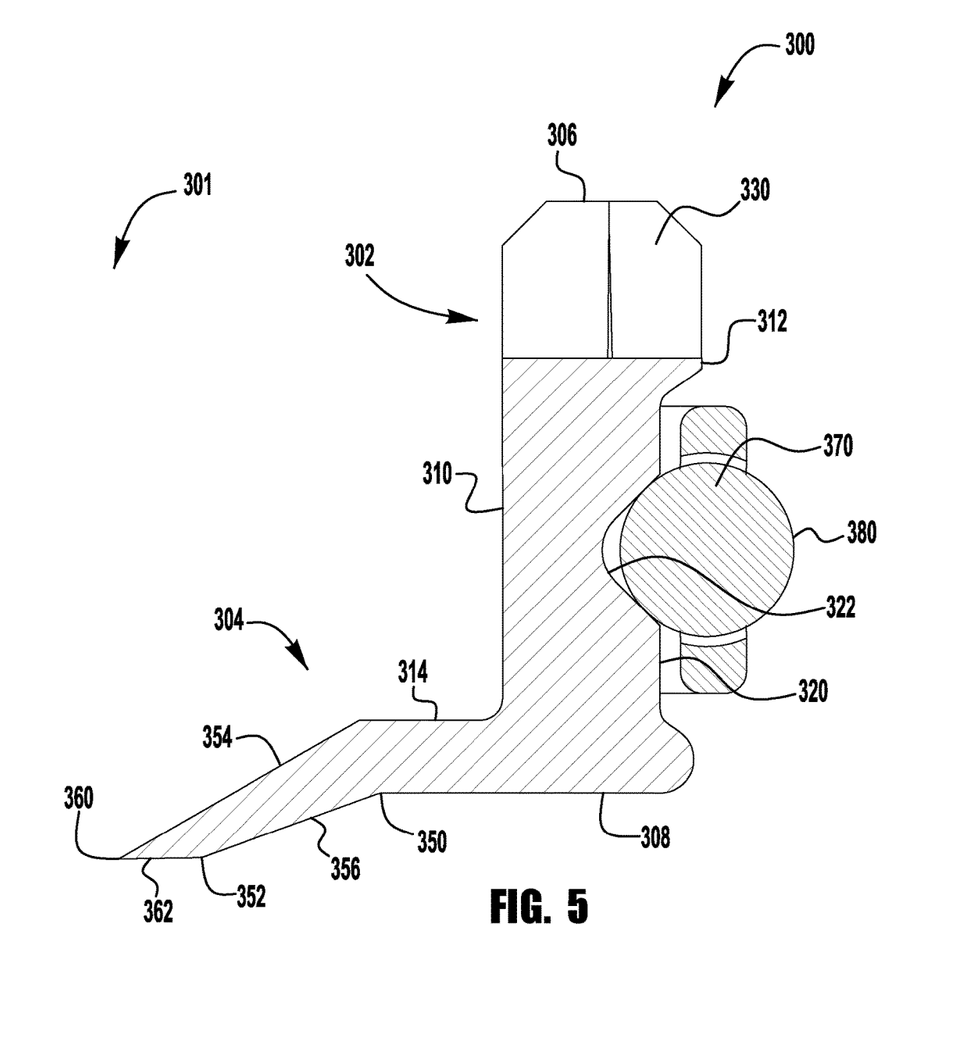
FIG. 5 is an enlarged view of a cross-section of rotary knife blade 300.

The rotary knife blade 300 includes an upper body portion 302 and a lower blade portion 304. The upper body portion 302 extends between an upper end 306 and a lower end 308, and includes an inner wall 310 and an outer wall 312. The outer wall 312 includes a bearing race 320 and an arcuate bearing surface 322 that extend radially inward into the outer wall 312 to receive a continuous rolling bearing structure 370. When assembled within the bearing race 320, the bearing structure 370 defines a convex outer surface 380 of the rotary knife blade 300 that projects radially outward from the outer wall 312. The continuous rolling bearing structure 370 supports the rotary knife blade 300 within the blade housing assembly 400. Specific details concerning the structure and configuration of the continuous rolling bearing structure 370 are disclosed in the '224 application and U.S. Pat. No. 8,806,761 (hereinafter "the '761 patent") filed on Jul. 25, 2011 and entitled Power Operated Rotary Knife, which is incorporated herein by reference in its entirety.

The bearing structure 370 is disposed in an annular gap 708 defined between opposing faces of the rotary knife blade 300, blade housing 410, and blade lock ring 450 of the blade housing assembly 400, in the region of the rotary knife blade bearing race 320. Specifically, the plurality of ball bearings (not shown) of the bearing structure 370 are disposed within an annular passageway 710, which is generally circular in cross section and defined by the opposing arcuate bearing surfaces 322, 417, and 457 of the rotary knife blade 300, blade housing 410, and lock ring 450, respectively.

The lower blade portion 304 of the rotary knife blade 300 extends from an upper end 350 to a lower end 352, and includes an inner wall 354 and a radially spaced apart outer wall 356. The inner and outer walls 354, 356 are generally frustoconical, converging in a direction proceeding downwardly toward the cutting edge 360 of the rotary knife blade 300. The inner wall 310 of the body portion 302 and the inner wall 354 of the blade portion 304 are connected by a shoulder surface 314 and combine to define an inner region 301 of the rotary knife blade 300. A bottom surface 362 defines the lower end 352 of the blade portion 304, connecting the inner and outer walls 354, 356. The cutting edge 360 is defined by the intersection of the bottom surface 362 and the inner wall 354 and is generally circular in nature. A plane aligned with the cutting edge 360 of the rotary knife blade 300 defines the cutting plane 702 of blade 300. The cutting angle 704 is defined as the acute angle between the inner wall 354 of the blade portion 304 and the cutting plane 702.

Figure 5A:
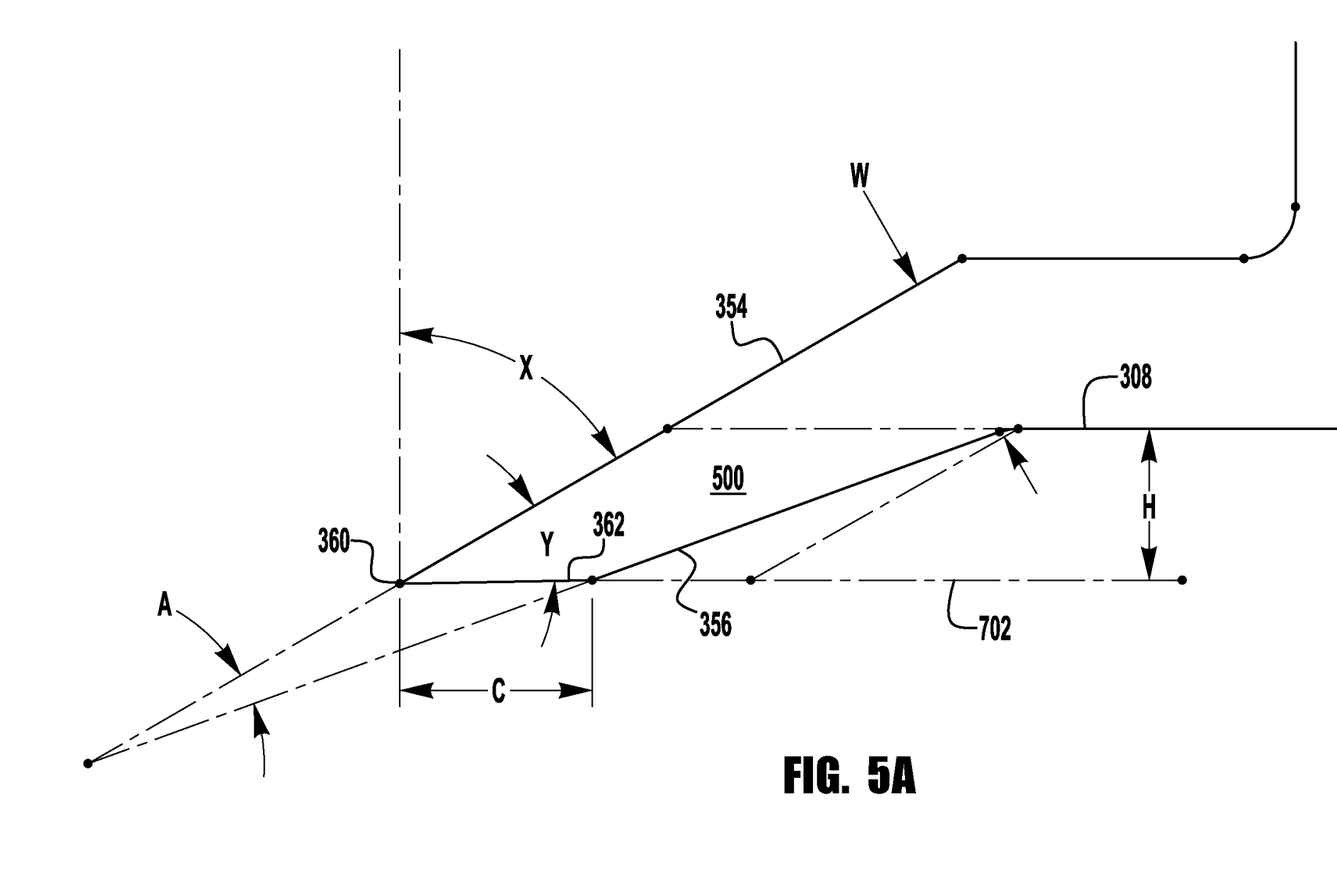
FIG. 5A is a schematic diagram of a portion of the cross-section of rotary knife blade 300 of FIG. 5.

The relationship between the various surfaces of the lower blade portion 304 is illustrated in FIG. 5A. Before the lower blade portion 304 of the rotary knife blade 300 is formed by a grinding operation, the thickness of the material W may range from about 0.005" to about 0.1". In one particular embodiment, the thickness of the material W is about 0.034". A height distance H from the cutting plane 702 to the lower end 308 of the upper body portion 302 of the rotary knife blade 300 may range from about 0.01" to about 1". In one particular embodiment, the height distance H is about 0.03".

A blade angle X between the inner wall 354 of the lower blade portion 304 and a vertical line extending from the cutting edge 360 may range from about 20 degrees to an angle approaching 90 degrees. In one particular embodiment, the blade angle X is about 60 degrees. The lower blade portion 304 is ground to bring the bottom surface 362 within a desirable range for a chisel grind width C, which may be up to about 0.106". In one particular embodiment, the chisel grind width C is about 0.037". In some other embodiments, the inner and outer walls 354, 356 are joined at the cutting edge 360 so that there is no bottom surface 362. To the extent that a bottom surface 362 exists in these other embodiments, the chisel grind width C is at most 0.001".

After these grinding operations, a taper angle A between the inner and outer walls 354, 356 is an acute angle, that is, it is greater than 0 and less than 90 degrees. In one particular embodiment, the taper angle A is about 10 degrees. The bottom surface 362 is then ground to a sharpened edge angle Y to create the cutting edge 360 and provide a bottom surface 362 that is more suitable for sliding over the skin of a patient during a cutting operation. The sharpened edge angle Y between the bottom surface 362 and the inner wall 354 is greater than 0 degrees and up to about 70 degrees. In one particular embodiment, the sharpened edge angle Y is about 29 degrees.

Figure 5B:
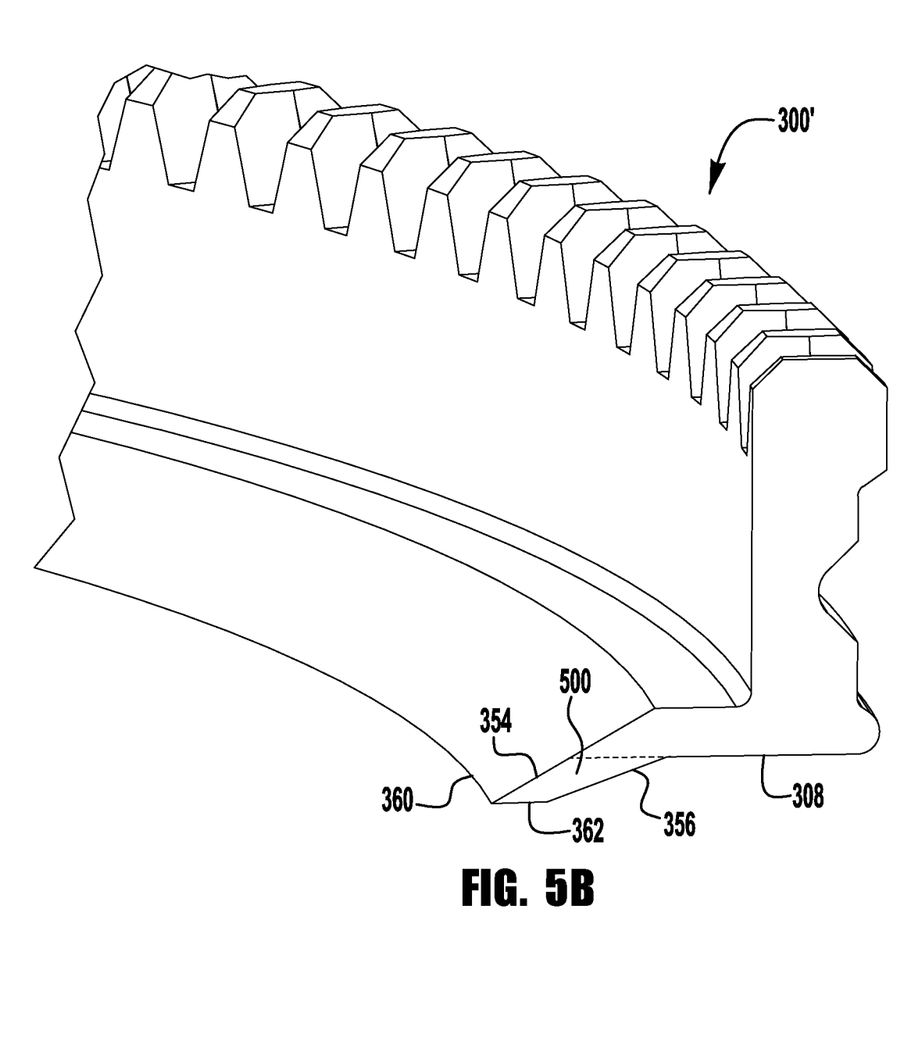
FIG. 5B is a perspective view of the cross-section of rotary knife blade 300 of FIG. 5.

As can be seen from FIG. 5A, the surfaces of the lower blade portion 304 form a quadrilateral shape 500 without any parallel sides that is bounded by the inner and outer walls 354, 356 of the lower blade portion 304, the bottom surface 362, and a line extending from the lower end 308 of the upper body portion 302. This shape is swept through a full revolution around the axis of rotation 700 to create the rotary knife blade 300. A partially swept shape is shown in FIG. 5B to illustrate how the surfaces of FIG. 5B form the blade 300. The dimensions noted above are maintained throughout the blade to ensure that all portions of the blade 300 are consistent in their cutting performance.

Figure 7:
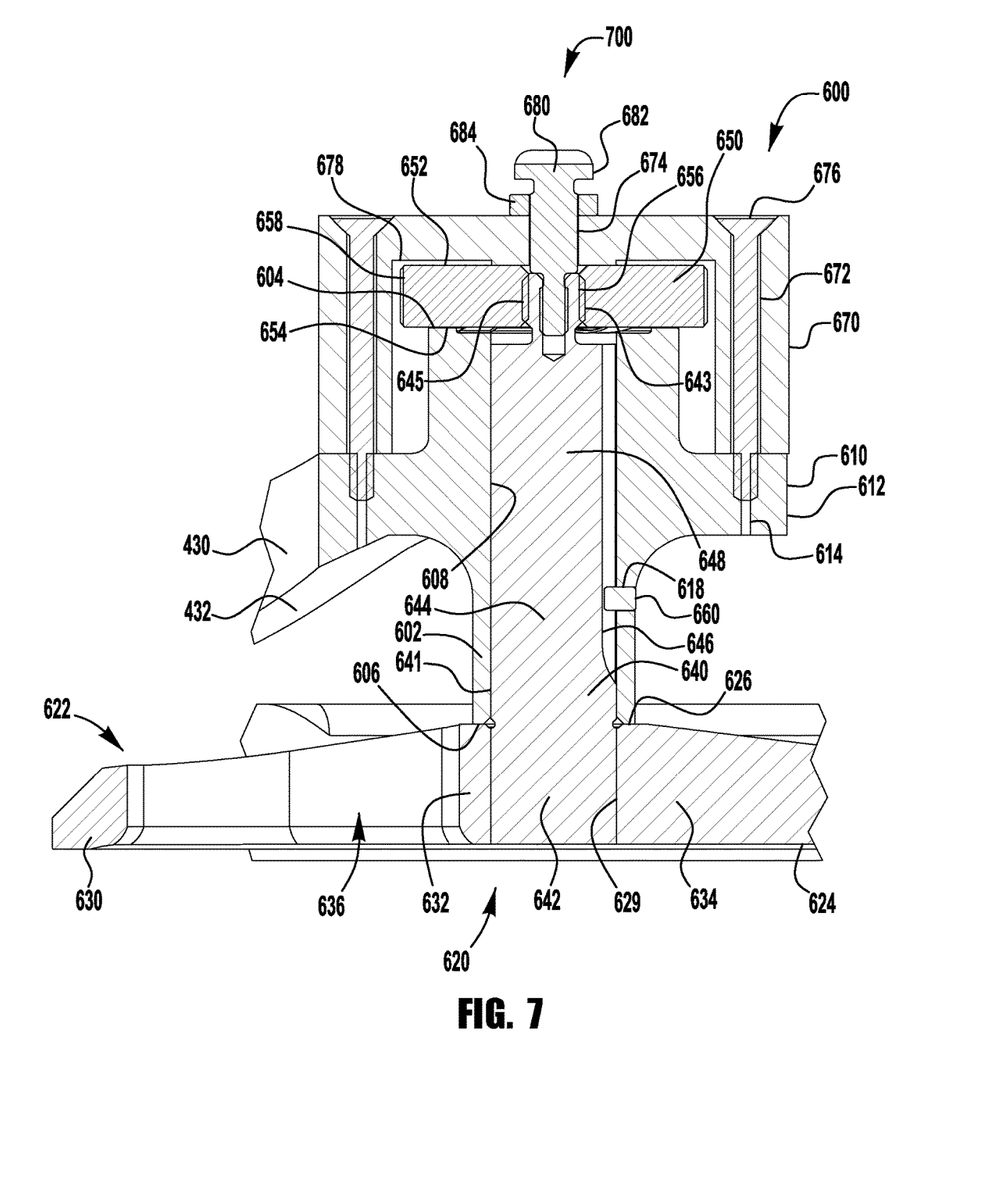
FIG. 7 is an enlarged view of a cross-section of depth gauge assembly 600.

The depth gauge assembly 600 includes a cylindrical depth gauge support 610 and the depth gauge 620. The depth gauge support 610 further includes a flange 612, a cylindrical support 602, and a stop plate 670. The depth gauge 620 includes a depth gauge plate 622, a shaft 640, and an adjustment knob 650. The depth gauge plate 622 is disposed within an inner region 301 of the blade 300. A depth of cut 706 is defined by the axial distance between the cutting plane 702 and the bottom surface 624 of the depth gauge plate 622. The depth of cut 706 determines the thickness of the skin excised by the dermatome 100 during use. As with the depth gauge of the '224 application, the depth gauge assembly 600 allows the operator to quickly and accurately change the depth of cut 706 during operation of the dermatome 100 by rotating the adjustment knob 650.

The depth gauge flange 612 extends from and is supported by the one or more ribs 432 of the blade housing support portion 430 and is generally rectangular, though it may be any shape. The cylindrical support 602 extends below the flange 612 to the lower end 606. The central bore 608 extends from the upper surface 604 of the flange 612 through the flange 612 and the cylindrical support 602 to the lower end 606. The depth gauge 620 includes the depth gauge plate 622 and the depth gauge shaft 640. The shaft 640 is slideably disposed within the central bore 608 and includes an outer surface 641, a lower end 642, a middle portion 644, and an upper end 648. The outer surface 641 of the shaft 640 includes a threaded adjustment portion 643 at the upper end 648 and an axially oriented slot 646. The upper end 648 includes a threaded opening 645 to receive a stop screw 680.

The stop plate 670 is generally rectangular and assembles to the depth gauge flange 612. The stop plate 670 includes an adjustment knob opening 678 that is configured to receive an adjustment knob 650 and limit vertical movement of the adjustment knob 650 when the depth of cut 706 is adjusted by an operator. The stop plate 670 further includes two openings 672 that are aligned with the threaded openings 614 in the depth gauge flange 612. Threaded fasteners 676 are inserted through the openings 672 and into the threaded openings 614 to secure the stop plate 670 to the flange 612. The stop plate 670 may be attached to the depth gauge flange 612 in any way, such as with clamps, pins, a welded connection, or the like.

The adjustment knob 650 is generally cylindrical and extends from the top surface 652 to the bottom surface 654. Upward movement of the adjustment knob 650 is limited by contact of the top surface 652 with the opening 678 in the stop plate 670, and downward movement of the adjustment knob 650 is limited by contact of the bottom surface 654 with the upper surface 604 of the flange 612. The knob 650 includes a threaded opening 656 for receiving a threaded adjustment portion 643 of the shaft 640. A peripheral surface 658 of the knob 650 includes a plurality of indentations to provide the operator with a better grip of the knob 650 when making adjustments to the depth of cut 706. An opening 618 in the cylindrical support 602 receives a dowel pin 660 that slideably engages the slot 646 of the shaft 640, preventing the shaft 640 from rotating as the adjustment knob 650 is rotated during adjustment of the depth of cut 706. As a result, rotational motion of the adjustment knob 650 is translated to linear vertical motion of the shaft 640 within the bore 608. The rotation of shaft 640 may be prevented by any means, such as with a keyed slot, using a non-circular shaft and bore, or the like. The top surface 652 of the knob 650 and the stop plate 670 include markings or indicia 653, 673 that indicate the current setting of the depth of cut 706, similar to those disclosed in the '224 application.

The stop plate 670 also includes a central opening 674 that is aligned with a stop screw opening 645 of the shaft 640. The stop screw 680 is inserted through the opening 674 and threaded into the threaded opening 645. The stop screw 680 includes a screw head 682 that engages a washer 684 placed on top of the stop plate 670. The position of the stop screw 680 sets the lower limit of the vertical movement of the depth gauge 620, and also prevents the threaded adjustment portion 643 of the shaft 640 from unthreading from the threaded portion 656 of the knob 650 during adjustment of the depth of cut 706. Compression of the washer 684 during downward adjustment of the knob 650 reduces backlash in the threaded connection between the knob 650 and the shaft 640. Alternatively, a biasing spring (not shown) like that shown in the '224 application may be used to limit thread backlash during adjustment of the depth of cut 706.

The depth gauge 620 includes a depth gauge plate 622 attached to the lower end 642 of the shaft 640. The gauge plate 622 includes a generally cylindrical center portion 632 and an annular ring portion 630 connected to the center portion 632 by one or more ribs 634. Openings 636 between the one or more ribs 634 allow an operator to view the skin below the dermatome 100 during a cutting operation. The center portion 632 includes a bore 628 that receives the lower end 642 of the shaft 640. The center portion 632 of the depth gauge plate 622 may be connected to the shaft 640 by any means, such as a threaded connection, a welded connection, a pinned connection, or the like. The bottom surface 624 of the annular ring portion 630 rests on the cutting surface during operation of the dermatome 100 to help an operator maintain the set depth of cut 706. Upward movement, and therefore maximum depth of cut, is limited by contact between the upper end 626 of the center portion 632 of the gauge plate 622 and the lower end 606 of the cylindrical support 602. Further details of the cutting operation of the dermatome 100 are disclosed in the '224 application.

Successful skin excising operations depend on precision equipment and operator skill. These variables are inversely related: the less precise the dermatome, the more skill and training an operator must have to perform the operation successfully. Skin removed from the patient for a typical skin grafting operation can be as thin as about 0.005 inches and as thick as about 0.043 inches. Dermatome 100 allows the operator to accurately excise skin at a desired thickness in a way that is less dependent on the operator's skill than prior dermatomes, resulting in more reliable results from operation to operation.

The position and size of the depth gauge relative to the cutting edge and depth of cut improves the precision and consistency of the depth of the cut. The relationship of the surfaces of the cutting portion of the blade also improve consistency and ease of cutting. For example, the sharpened edge angle between the bottom surface of the blade and the inner wall of the lower blade portion provides relief behind the cutting edge of the blade, thereby reducing friction between the blade and the skin of the patient, helping to separate the excised skin from uncut skin. The angle of the bottom surface improves movement of the dermatome during a cutting operation so that the dermatome can be moved at a consistent and predictable speed across the body of the patient while removing an excised portion of skin with substantially uniform thickness at a given setting. The movement of the cutting edge is countered by the depth gauge pressing against the body of the patient, resulting in a precise and repeatable cutting of the skin during an excision operation. That is, the same setting of the adjustment knob will result in the same thickness of excised skin between operations.

Additionally, features of dermatome 100 critical to precision cutting can be machined during a single manufacturing operation, improving alignment of critical features and components. This is accomplished by the generally cylindrical shape of key components of dermatome 100.

Components of the power operated dermatome disclosed in the '224 application that are similar to the upper body portion 302 of the rotary knife blade 300, blade housing 410, and lock ring 450 are generally frustoconical in shape. In the power operated dermatome 100, however, these components have a generally cylindrical shape. Consequently, manufacturability of the blade 300, blade housing 410, and lock ring 450 is improved compared to similar components of the dermatome of the '224 application. For example, the generally cylindrical shape of the blade housing 410 allows features critical to the operation of the dermatome 100, such as the annular blade channel 416 and arcuate bearing surface 417, to be machined in a single operation resulting in more precise positioning of these features relative to each other. A skin deflector 444 can also be integrally formed into the blade housing 410 because of the blade housing's 410 generally cylindrical shape. Forming the skin deflector 444 during the same operation as the blade channel 416 results in improved alignment of the rotary knife blade 300 and the skin deflector 444, allowing excised skin to more smoothly transition from the surface of the blade 300 to the skin deflector 444.

The generally cylindrical shape of these components also increases their stiffness relative to generally frustoconical components. This increased stiffness provides blade 300 with greater resistance to warping during heat treatment of cutting edge 360, thereby improving the quality of the component and manufacturing yield.

Manufacturing advantages of generally cylindrical parts extend to the time and cost of manufacturing the components as well. For example, blade 300 can be machined from a blank formed with a stamping process that is closer to the final dimensions of the part and does not require a special chuck during machining. As a result, blade 300 is produced in less time and for lower cost than the generally frustoconical blade of the dermatome of the '224 application. Integrally forming skin deflector 444 as part of blade housing 410 also reduces manufacturing time and cost by reducing the number of components of dermatome 100.

The generally cylindrical shape of blade 300, blade housing 410, and lock ring 450 also improves handling and performance of power operated dermatome 100. The cylindrical shape of these components allows head assembly 200 to be smaller than the head assembly of the dermatome disclosed in the '224 application without reducing the diameter of cutting edge 360 of blade 300. The smaller overall size of dermatome 100 as compared to the dermatome of the '224 application provides many benefits. For example, head assembly 200 of dermatome 100 weighs less than that disclosed in the '224 application, allowing for improved maneuverability during operation. Also, the radial distance between cutting edge 360 and outer surface 455 of lock ring 450 allows an operator to excise skin closer to joints or transitions in the body than the dermatome of the '224 application.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Moreover, elements described with one embodiment may be readily adapted for use with other embodiments. Therefore, the invention, in its broader aspects, is not limited to the specific details, the representative apparatus and illustrative examples shown and described. Accordingly, departures may be made from such details without departing from the spirit or scope of the applicants' general inventive concept.

What is claimed is:

1. A power operated dermatome comprising:
a blade housing having a skin deflector to prevent excised skin from tearing as it is removed from the dermatome;
an annular rotary knife blade supported for rotation about an axis of rotation by the blade housing, the annular rotary knife blade having an inner region and comprising:
an upper body portion including an inner wall and a radially spaced apart outer wall and an upper end and an axially spaced apart lower end, the outer wall of the upper body portion including a bearing race extending radially inwardly into the outer wall, the upper end of the upper body portion including a driven gear; and a lower blade portion extending from the upper body portion, the lower blade portion including an inner wall and a radially spaced apart outer wall and an upper end and an axially spaced apart lower end, a bottom surface of the lower blade portion extending along the lower end of the lower blade portion, an intersection of the bottom surface and the inner wall of the lower blade portion forming a cutting edge of the annular rotary knife blade, the inner wall and the outer wall of the lower blade portion converging in a direction proceeding toward the cutting edge;

wherein the inner wall of the lower blade portion and the inner wall of the upper body portion are radially spaced apart, and at the upper end of the lower blade portion, are connected by a shoulder surface that extends transversely to the axis of rotation of the annular rotary knife blade.

2. A rotary knife blade assembly rotatable about a central axis of rotation in a power operated dermatome, the rotary knife blade assembly comprising:

a rotary knife blade comprising:

an upper body portion including an inner wall and a radially spaced apart outer wall and an upper end and an axially spaced apart lower end, the outer wall of the upper body portion including a bearing race extending radially inwardly into the outer wall, the upper end of the upper body portion including a driven gear; and a lower blade portion extending from the upper body portion, the lower blade portion including an inner wall and a radially spaced apart outer wall and an upper end and an axially spaced apart lower end, a bottom surface of the lower blade portion extending along the lower end of the lower blade portion, an intersection of the bottom surface and the inner wall of the lower blade portion forming a cutting edge of the rotary knife blade, the inner wall and the outer wall of the lower blade portion converging in a direction proceeding toward the cutting edge;

wherein the inner wall of the lower blade portion and the inner wall of the upper body portion are radially spaced apart and connected by a shoulder surface that extends transversely to the central axis of rotation of the rotary knife blade, the inner wall of the lower blade portion being substantially planar between the cutting edge and the shoulder surface; and a continuous rolling bearing structure in contact with the bearing race of the outer wall of the upper body portion of the rotary knife blade, the continuous rolling bearing structure forming a convex outer surface of the rotary knife blade assembly and projecting radially outwardly from the outer wall of the upper body portion of the rotary knife blade.

3. The rotary knife blade assembly of claim 2 wherein the inner and outer walls of the lower blade portion of the rotary knife blade are frustoconical.

4. The rotary knife blade assembly of claim 2 wherein the shoulder surface that connects the inner wall of the lower blade portion and the inner wall of the upper body portion of the rotary knife blade extends orthogonally to the central axis of rotation of the rotary knife blade.

5. The rotary knife blade assembly of claim 2 wherein the shoulder surface that connects the inner wall of the lower blade portion and the inner wall of the upper body portion of the rotary knife blade is substantially planar.

6. A rotary knife blade assembly rotatable about a central axis of rotation in a power operated dermatome, the rotary knife blade assembly comprising:

a rotary knife blade comprising:

an upper body portion including an inner wall and a radially spaced apart outer wall and an upper end and an axially spaced apart lower end, the outer wall of the upper body portion including a bearing race extending radially inwardly into the outer wall, the upper end of the upper body portion including a driven gear; and a lower blade portion extending from the upper body portion, the lower blade portion including an inner wall and a radially spaced apart outer wall and an upper end and an axially spaced apart lower end, a bottom surface of the lower blade portion extending along the lower end of the lower blade portion, an intersection of the bottom surface and the inner wall of the lower blade portion forming a cutting edge of the rotary knife blade, the inner and outer wall converging in a direction proceeding toward the bottom surface of the lower blade portion;

wherein the inner wall of the lower blade portion and the inner wall of the upper body portion are radially spaced apart and connected by a shoulder surface that extends transversely to the central axis of rotation of the rotary knife blade, the inner wall of the lower blade portion being substantially planar between the cutting edge and the shoulder surface; and a continuous rolling bearing structure in contact with the bearing race of the outer wall of the upper body portion of the rotary knife blade, the continuous rolling bearing structure forming a convex outer surface of the rotary knife blade assembly and projecting radially outwardly from the outer wall of the upper body portion of the rotary knife blade.

7. The rotary knife blade assembly of claim 6 wherein the inner and outer walls of the lower blade portion of the rotary knife blade are frustoconical.

8. The rotary knife blade assembly of claim 6 wherein the shoulder surface that connects the inner wall of the lower blade portion and the inner wall of the upper body portion of the rotary knife blade extends orthogonally to the central axis of rotation of the rotary knife blade.

9. The rotary knife blade assembly of claim 6 wherein the shoulder surface that connects the inner wall of the lower blade portion and the inner wall of the upper body portion of the rotary knife blade is substantially planar.

10. A rotary knife blade assembly rotatable about a central axis of rotation in a power operated dermatome, the rotary knife blade assembly comprising:

a rotary knife blade comprising:

an upper body portion including an inner wall and a radially spaced apart outer wall and an upper end and an axially spaced apart lower end, the outer wall of the upper body portion including a bearing race extending radially inwardly into the outer wall, the upper end of the upper body portion including a driven gear; and a lower blade portion extending from the upper body portion, the lower blade portion including an inner wall and a radially spaced apart outer wall and an upper end and an axially spaced apart lower end, a bottom surface of the lower blade portion extending along the lower end of the lower blade portion, an intersection of the bottom surface and the inner wall of the lower blade section forming a cutting edge of the rotary knife blade and defining a cutting plane of the rotary knife blade, the bottom surface of the lower blade portion extending along the cutting plane of the rotary knife blade;

wherein the inner wall of the lower blade portion and the inner wall of the upper body portion are radially spaced apart and connected by a shoulder surface that extends transversely to the central axis of rotation of the rotary knife blade, the inner wall of the lower blade portion being substantially planar between the cutting edge and the shoulder surface; and a continuous rolling bearing structure in contact with the bearing race of the outer wall of the upper body portion of the rotary knife blade, the continuous rolling bearing structure forming a convex outer surface of the rotary knife blade assembly and projecting radially outwardly from the outer wall of the upper body portion of the rotary knife blade.

11. The rotary knife blade assembly of claim 10 wherein the inner wall and the outer wall of the lower blade portion converge in a direction proceeding toward the bottom surface of the lower blade portion.

12. The rotary knife blade assembly of claim 10 wherein the inner and outer walls of the lower blade portion of the rotary knife blade are frustoconical.

13. The rotary knife blade assembly of claim 10 wherein the shoulder surface that connects the inner wall of the lower blade portion and the inner wall of the upper body portion of the rotary knife blade extends orthogonally to the central axis of rotation of the rotary knife blade.

14. The rotary knife blade assembly of claim 10 wherein the shoulder surface that connects the inner wall of the lower blade portion and the inner wall of the upper body portion of the rotary knife blade is substantially planar.

15. A rotary knife blade rotatable about a central axis of rotation in a power operated dermatome, the rotary knife blade comprising:

an upper body portion including an inner wall and a radially spaced apart outer wall and an upper end and an axially spaced apart lower end, the outer wall of the upper body portion including a bearing race extending radially inwardly into the outer wall, the upper end of the upper body portion including a driven gear; and a lower blade portion extending from the upper body portion, the lower blade portion including an inner wall and a radially spaced apart outer wall and an upper end and an axially spaced apart lower end, a bottom surface of the lower blade portion extending along the lower end of the lower blade portion, an intersection of the bottom surface and the inner wall of the lower blade portion forming a cutting edge of the rotary knife blade, the inner wall and the outer wall of the lower blade portion converging in a direction proceeding toward the cutting edge;

wherein the inner wall of the lower blade portion and the inner wall of the upper body portion are radially spaced apart and connected by a shoulder surface that extends transversely to the central axis of rotation of the rotary knife blade, the inner wall of the lower blade portion being substantially planar between the cutting edge and the shoulder surface.

16. The rotary knife blade of claim 15 wherein the inner and outer walls of the lower blade portion of the rotary knife blade are frustoconical.

17. The rotary knife blade of claim 15 wherein the shoulder surface that connects the inner wall of the lower blade portion and the inner wall of the upper body portion of the rotary knife blade extends orthogonally to the central axis of rotation of the rotary knife blade.

18. The rotary knife blade of claim 15 wherein the shoulder surface that connects the inner wall of the lower blade portion and the inner wall of the upper body portion of the rotary knife blade is substantially planar.

19. A rotary knife blade rotatable about a central axis of rotation in a power operated dermatome, the rotary knife blade comprising:

an upper body portion including an inner wall and a radially spaced apart outer wall and an upper end and an axially spaced apart lower end, the outer wall of the upper body portion including a bearing race extending radially inwardly into the outer wall, the upper end of the upper body portion including a driven gear; and a lower blade portion extending from the upper body portion, the lower blade portion including an inner wall and a radially spaced apart outer wall and an upper end and an axially spaced apart lower end, a bottom surface of the lower blade portion extending along the lower end of the lower blade portion, an intersection of the bottom surface and the inner wall of the lower blade portion forming a cutting edge of the rotary knife blade, the inner and outer walls of the lower blade portion converging in a direction proceeding toward the bottom surface of the lower blade portion;

wherein the inner wall of the lower blade portion and the inner wall of the upper body portion are radially spaced apart and connected by a shoulder surface that extends transversely to the central axis of rotation of the rotary knife blade, the inner wall of the lower blade portion being substantially planar between the cutting edge and the shoulder surface.

20. The rotary knife blade of claim 19 wherein the inner and outer walls of the lower blade portion of the rotary knife blade are frustoconical.

21. The rotary knife blade of claim 19 wherein the shoulder surface that connects the inner wall of the lower blade portion and the inner wall of the upper body portion of the rotary knife blade extends orthogonally to the central axis of rotation of the rotary knife blade.

22. The rotary knife blade of claim 19 wherein the shoulder surface that connects the inner wall of the lower blade portion and the inner wall of the upper body portion of the rotary knife blade is substantially planar.

23. A rotary knife blade rotatable about a central axis of rotation in a power operated dermatome, the rotary knife blade comprising:

an upper body portion including an inner wall and a radially spaced apart outer wall and an upper end and an axially spaced apart lower end, the outer wall of the upper body portion including a bearing race extending radially inwardly into the outer wall, the upper end of the upper body portion including a driven gear; and a lower blade portion extending from the upper body portion, the lower blade portion including an inner wall and a radially spaced apart outer wall and an upper end and an axially spaced apart lower end, a bottom surface of the lower blade portion extending along the lower end of the lower blade portion, an intersection of the bottom surface and the inner wall of the lower blade section forming a cutting edge of the rotary knife blade and defining a cutting plane of the rotary knife blade, the bottom surface of the lower blade portion extending along the cutting plane of the rotary knife blade;

wherein the inner wall of the lower blade portion and the inner wall of the upper body portion are radially spaced apart and connected by a shoulder surface that extends transversely to the central axis of rotation of the rotary knife blade, the inner wall of the lower blade portion being substantially planar between the cutting edge and the shoulder surface.

24. The rotary knife blade of claim 23 wherein the inner wall and outer wall of the lower blade portion converge in a direction proceeding toward the bottom surface of the lower blade portion.

25. The rotary knife blade of claim 23 wherein the inner and outer walls of the lower blade portion of the rotary knife blade are frustoconical.

26. The rotary knife blade of claim 23 wherein the shoulder surface that connects the inner wall of the lower blade portion and the inner wall of the upper body portion of the rotary knife blade extends orthogonally to the central axis of rotation of the rotary knife blade.

27. The rotary knife blade of claim 23 wherein the shoulder surface that connects the inner wall of the lower blade portion and the inner wall of the upper body portion of the rotary knife blade is substantially planar.

28. A rotary knife blade assembly rotatable about a central axis of rotation in a power operated dermatome, the rotary knife blade assembly comprising:
 a rotary knife blade comprising:
  an upper body portion including an inner wall and a radially spaced apart outer wall and an upper end and an axially spaced apart lower end, the outer wall of the upper body portion including a bearing race extending radially inwardly into the outer wall, the upper body portion including a driven gear; and
  a lower blade portion extending from the upper body portion, the lower blade portion including an inner wall and a radially spaced apart outer wall and an upper end and an axially spaced apart lower end, a bottom surface of the lower blade portion extending along the lower end of the lower blade portion, an intersection of the bottom surface and the inner wall of the lower blade portion forming a cutting edge of the rotary knife blade, the inner and outer walls converging in a direction proceeding toward the bottom surface of the lower blade portion;
  wherein the inner walls of the lower blade portion and the inner wall of the upper body portion are radially spaced apart and connected by a shoulder surface extending transversely to the central axis of rotation of the rotary knife blade and at least a portion of the inner wall of the upper body portion extending substantially parallel to the central axis of rotation of the rotary knife blade; and
 a continuous rolling bearing structure in contact with the bearing race of the outer wall of the upper body portion of the upper body portion of the rotary knife blade, the continuous rolling bearing structure forming a convex outer surface of the rotary knife blade assembly and projecting radially outwardly from the outer wall of the upper body portion of the rotary knife blade.

29. A rotary knife blade rotatable about a central axis of rotation in a power operated dermatome, the rotary knife blade comprising:
 an upper body portion including an inner wall and a radially spaced apart outer wall and an upper end and an axially spaced apart lower end, the outer wall of the upper body portion including a bearing race extending radially inwardly into the outer wall, the upper body portion including a driven gear; and
 a lower blade portion extending from the upper body portion, the lower blade portion including an inner wall and a radially spaced apart outer wall and an upper end and an axially spaced apart lower end, a bottom surface of the lower blade portion extending along the lower end of the lower blade portion, an intersection of the bottom surface and the inner wall of the lower blade portion forming a cutting edge of the rotary knife blade, the inner and outer walls converging in a direction proceeding toward the bottom surface of the lower blade portion;
 wherein the inner wall of the lower blade portion and the inner wall of the upper body portion are radially spaced apart and are connected by a shoulder surface extending transversely to the central axis of rotation of the rotary knife blade and at least a portion of the inner wall of the upper body portion extending substantially parallel to the central axis of rotation of the rotary knife blade.

* * * * *